US006927313B2

(12) United States Patent
Bianchini et al.

(10) Patent No.: US 6,927,313 B2
(45) Date of Patent: Aug. 9, 2005

(54) PROCESS FOR THE SELECTIVE OLIGOMERIZATION OF ETHYLENE

(75) Inventors: Claudio Bianchini, Florence (IT); Anna Sommazzi, Santa Margherita Ligure-Genova (IT); Giuseppe Mantovani, Finale Emilia-Modena (IT); Roberto Santi, Novara (IT); Francesco Masi, Sant'Angelo Lodigiano-Lodi (IT)

(73) Assignee: Polimeri Europa S.p.A., Brindisi (IT)

( * ) Notice: Subject to any disclaimer, the term of this patent is extended or adjusted under 35 U.S.C. 154(b) by 128 days.

(21) Appl. No.: 10/399,982

(22) PCT Filed: Oct. 3, 2001

(86) PCT No.: PCT/EP01/11407

§ 371 (c)(1),
(2), (4) Date: Oct. 1, 2003

(87) PCT Pub. No.: WO02/34701

PCT Pub. Date: May 2, 2002

(65) Prior Publication Data

US 2004/0059074 A1 Mar. 25, 2004

(30) Foreign Application Priority Data

Oct. 26, 2000 (IT) .................................... MI2000A2320

(51) Int. Cl.$^7$ ............................ C07C 2/04; C08F 4/602
(52) U.S. Cl. ..................... 585/515; 585/526; 526/161; 526/171; 526/172; 526/348; 502/155; 502/167

(58) Field of Search ................................. 585/515, 512, 585/511, 526; 526/161, 171, 172, 348; 502/155, 167

(56) References Cited

U.S. PATENT DOCUMENTS 5,880,323 A * 3/1999 Brookhart et al. .......... 585/527
5,932,670 A * 8/1999 Koppl et al. ................ 526/161

OTHER PUBLICATIONS

B.L. Small et al.: "Iron–based catalysts with exceptionally high activities and selectivites for oligomerization of ethylene to linear alpha–olefins" Journal of the Americal Chemical Society, vol. 120, No. 28, pp. 7143–7144.

* cited by examiner

Primary Examiner—Robert D. Harlan
(74) Attorney, Agent, or Firm—Oblon, Spivak, McClelland, Maier & Neustadt, P.C.

(57) ABSTRACT

Process for the selective oligomerization of ethylene to give α-olefins essentially consisting of $C_4$ to $C_8$, characterized in that it is carried out in the presence of a catalytic system comprising the complex having general formula (II): $(L)M(Y)_n$ wherein L represents the ligand having general formula (I) M represents a transition metal; Y is selected from groups of an anionic nature bound to the metal as anion in ionic couple or with a covalent bond of the "σ" type.

12 Claims, No Drawings

PROCESS FOR THE SELECTIVE OLIGOMERIZATION OF ETHYLENE

Linear alpha-olefins represent an important petrochemical material. Their applications range from their use as comonomers for polyethylene, to plasticizers, synthetic lubricants and detergent alcohols. Their applications depend on the number of carbon atoms as indicated below:
$C_4$–$C_8$ as comonomers for polyethylene
$C_6$–$C_{10}$ as plasticizers
$C_{10}$–$C_{12}$ as synthetic lubricants
$C_{12}$–$C_{18}$ as detergents The possible oligomerization of ethylene to 1-hexene, 1-octene and also 1-butene to be used as comonomers for ethylene copolymers seems to be of interest, due to the great demand for these monomers.

For the oligomerization of ethylene U.S. Pat. No. 3,644,563 (Shell) uses homogeneous catalysts based on organometallic complexes of nickel, with a ligand (P∩O) on which the catalytic activity and selectivity depend. The catalytic precursor is prepared at 40° C. by the reaction of $NiCl_2$ and a bidentate ligand P—O (such as for example diphenylphosphinoacetic acid and diphenylphosphinobenzoic acid) in the presence of ethylene (87 bars) and a reducing agent such as $NaBH_4$. The oligomerization, on the other hand, is carried out at 120° C. and 140 bars. The olefins obtained according to this process have a high linearity and their molecular weights follow a Shulz Flory distribution.

This process therefore has the disadvantage of requiring rather drastic pressure and temperature conditions, and of giving a wide distribution of α-olefins.

U.S. Pat. No. 4,783,573 (Idemitsu) describes a process in which ethylene is oligomerized at 33 bars and 120° C. in the presence of a catalytic system which comprises $ZrCl_4$, aluminum alkyls and a Lewis base. The olefins obtained are mainly $C_6$–$C_8$ with a selectivity higher than 90%.

This system also has the disadvantage of requiring high temperatures and pressures.

EP-A-668,106 (Phillips) describes catalytic systems based on chromium(III)alkanoates, which are generally activated with aluminum alkyl $Al(Et)_3$ mixed with $AlCl(Et)_2$, in the presence of a pyrrole, or one of its alkaline salts, and a halogenating agent, preferably $GeCl_4$, used at temperatures of about 100° C. with ethylene pressures higher than 40 atm. These chromium catalytic systems protems produce hexene-1 with a selectivity of over 99% and a high activity only at a high ethylene pressure, as polyethylene is obtained at low pressures.

M. Brookhart and B. L. Small (J.A.C.S. 120, 7143, 1998) recently described iron complexes containing trinitrogenated pyridine di-iminic ligands

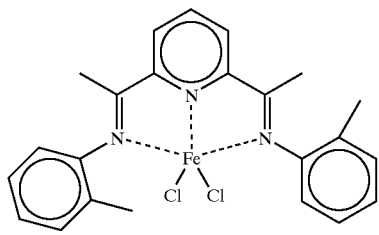

which have proved to be active catalysts in the oligomerization of ethylene to olefins. The catalysts are activated by MAO and function at a temperature ranging from 25 to 60° C., at pressures ranging from 1 to 40 atm. The complex has an hourly turnover (TOF) of $1.0 \times 10^5$ at 25° C. and 1 atm. With this catalytic system $C_4$–$C_{16}$ and higher oligomers (wax formations) are obtained. This system therefore has the disadvantage of having a low selectivity.

A process has now been found for the production of prevalently $C_4$–$C_8$ α-olefins which overcomes the drawbacks mentioned above.

In accordance with this, the present invention relates to a process for the selective oligomerization of ethylene to give essentially $C_4$–$C_8$ α-olefins, characterized in that it is carried out in the presence of a catalytic system comprising the complex having general formula (II)

wherein
L represents the ligand having general formula (I)

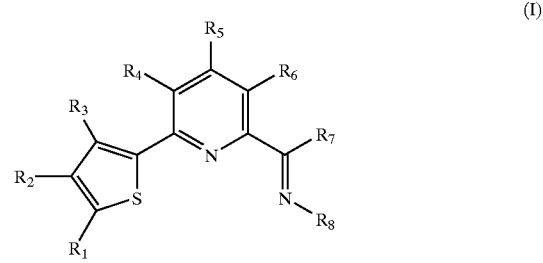

wherein $R_1$, $R_2$, $R_3$, $R_4$, $R_5$, $R_6$, the same or different, are selected from hydrogen, halogen, $C_1$–$C_{10}$ alkyl, $C_6$–$C_{15}$ aryl optionally halogenated, or adjacent pairs of $R_i$ groups (with i ranging from 1 to 6) are bound to each other to give cyclic hydrocarbon structures condensed with the thiophene or pyridine ring;
$R_7$ is selected from H, $C_1$–$C_{10}$ alkyl, $C_6$–$C_{15}$ aryl;
$R_8$ is selected from $C_1$–$C_{10}$ alkyl and $C_6$–$C_{15}$ aryl;
M is a metal selected from transition metals, i.e. metals of groups 3 to 12, preferably from 4 to 10, of the periodic table, and lanthanides; even more preferably from Iron and Cobalt; the above metal M being in oxidation state "s" positive different from zero, generally between 1 and 4;
Y is selected from groups of an anionic nature bound to the metal as anion in ionic couple or with a covalent bond of the "σ" type; Y is preferably selected from chlorine, bromine, alkoxide and carboxylate (having from 2 to 15 carbon atoms);
n expresses the number of Y groups sufficient for neutralizing the formal oxidation charge "s" of the metal M.

The preparation of the complexes having general formula (II) and the ligands having general formula (I) is described in the co-pending patent filed by the same applicant.

The catalytic system used in the process of the present invention comprises the presence, in addition to the complex having general formula (II), of a cocatalyst, compound (B), essentially consisting of at least one organic compound of an element M' different from carbon and selected from elements of groups 2, 12, 13 or 14 of the periodic table as defined above.

In particular, according to the present invention, said element M' is selected from boron, aluminum, zinc, magnesium, gallium and tin, more particularly boron and aluminum.

In a preferred embodiment of the present invention, the cocatalyst (B) is an organo-oxygenated derivative of aluminum, gallium or tin. This can be defined as an organic compound of M', wherein the latter is bound to at least one oxygen atom and at least one organic group consisting of an alkyl group having from 1 to 6 carbon atoms, preferably methyl.

According to this aspect of the invention, the cocatalyst is more preferably an aluminoxane. As is known, aluminoxanes are compounds containing Al—O—Al bonds, with a varying O/Al ratio, obtained in the art by reaction, under controlled conditions, of an aluminum alkyl, or aluminum alkyl halide, with water or other compounds containing pre-determined quantities of water available, as for example, in the case of the reaction of aluminum trimethyl with aluminum sulfate hexahydrate, copper sulfate pentahydrate or iron sulfate pentahydrate. Aluminoxanes which are preferably used for the formation of the polymerization catalyst of the present invention are cyclic and/or linear, oligo- or polymeric compounds, characterized by the presence of repetition units having the following formula:

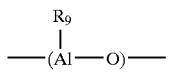

wherein $R_9$ is a $C_1$–$C_6$ alkyl group, preferably methyl.

Each aluminoxane molecule preferably contains from 4 to 70 repetitive units which are not necessarily all the same, but may contain different $R_9$ groups.

Said aluminoxanes, and particularly methylaluminoxane are compounds which can be obtained with known organometallic chemical processes, for example by the addition of aluminum trimethyl to a suspension in hexane of aluminum sulfate hydrate.

When used for the formation of a polymerization catalyst according to the present invention, the aluminoxanes are put in contact with a complex having formula (II) in such proportions that the atomic ratio between Al and the metal M is within the range of 10 to 10,000 and preferably from 100 to 5,000. The sequence with which the complex (II) and the aluminoxane (B) are put in contact with each other, is not particularly critical.

In addition to the above preferred aluminoxanes, the definition of component (B) according to the present invention also comprises galloxanes (in which, in the previous formulae, gallium is present instead of aluminum) and stannoxanes, whose use as cocatalysts for the polymerization of olefins in the presence of metallocene complexes is known, for example, from patents U.S. Pat. Nos. 5,128,295 and 5,258,475.

According to another preferred aspect of the present invention, said catalyst can be obtained by putting component (A) consisting of at least on complex having formula (II), in contact with the cocatalyst (B) consisting of at least one compound or a mixture of organometallic compounds of M' capable of reacting with the complex having formula (II), extracting from this, a σ-bound group Y as defined above, to form, on the one side at least one neutral compound, and on the other side an ionic compound consisting of a cation containing the metal M coordinated to the ligand L, and an organic non-coordinating anion containing the metal M', whose negative charge is delocalized on a multicentric structure.

Components (B) suitable as ionizing systems of the above type are preferably selected from voluminous organic compounds of aluminum and especially of boron, such as for example, those represented by the following general formulae:

[($R_C$)$_w$H$_{4-w}$]o[B($R_D$)$_4$]⁻;

B($R_D$)$_3$;

[Ph$_3$C]⁺o[B($R_D$)$_4$]⁻;

[($R_C$)$_3$PH]⁺o[B($R_D$)$_4$]⁻;

[Li]⁺o[B($R_D$)$_4$]⁻;

[Li]⁺o[Al($R_D$)$_4$]⁻;

wherein the deponent "w" is an integer ranging from 0 to 3, each $R_C$ group independently represents an alkyl or aryl radical having from 1 to 10 carbon atoms and each $R_D$ group independently represents an aryl radical partially or, preferably, totally fluorinated, having from 6 to 20 carbon atoms.

Said compounds are generally used in such quantities that the ratio between the atom M' in component (B) and the atom M in the complex having formula (II) is within the range of 0.1 to 15, preferably from 0.5 to 10, more preferably from 1 to 6.

Component (B) can consist of a single compound, normally an ionic compound, or, especially when no Y in the compound having formula (II) is an alkyl, a combination of this compound with an alkylating agent such as MAO, or, preferably, with an aluminum trialkyl having from 1 to 8 carbon atoms in each alkyl residue, such as for example AlMe$_3$, AlEt$_3$, Al(i-Bu)$_3$, according to what is specified above.

In general, the formation of the ionic-type catalytic system, in accordance with this latter aspect of the present invention, is preferably carried out in an inert liquid medium, more preferably hydrocarbon. The selection of components (A) and (B), which are preferably combined with each other, as well as the particular method used, can vary depending on the molecular structures and result desired, according to what is analogously described in specific literature available to experts in the field for other complexes of transition metals with imine binders, for example by L. K. Johnson et al. in the publication "Journal of the American Chemical Society, vol. 117 (1995), pages 6414–6415, and by G. van Koten and K. Vrieze in "Advances in Organometallic Chemistry, vol. 21, page 151".

Examples of these methods are qualitatively schematized in the list provided hereunder, which however does not limit the overall scope of the present invention:

($m_1$) by contact of a complex having the previous general formula (II), wherein at least one ligand Y is hydrogen or an alkyl radical, with an ionic compound whose cation is capable of reacting with one of said substituents to form a neutral compound, and whose anion is voluminous, non-coordinating and capable of delocalizing the negative charge;

($m_2$) by the reaction of a complex having the previous formula (II) with an alkylating agent, preferably an aluminum trialkyl, used in molar excess of 10/1 to 300/1, followed by the reaction with a strong Lewis acid, such as for example, tris(pentafluorophenyl) boron in a more or less stoichiometric quantity or in slight excess with respect to the metal M;

($m_3$) by contact and reaction of a complex having the previous formula (II) with a molar excess of 10/1 to 1000/1, preferably from 100/1 to 500/1 of an aluminum trialkyl or an alkylaluminum halide represented by the formula AlR'''$_m$Z$_{3-m}$, wherein R''' is a linear or branched $C_1$–$C_8$ alkyl group, or one of their mixtures, Z is a halogen, preferably chlorine or bromine, and "m" is a decimal number ranging from 1 to 3; followed by the addition to the composition thus obtained, of at least one ionic compound of the type described above in such quantities that the ratio between B or Al in the ionic compound and the atom M is within the range of 0.1 to 15, preferably from 1 to 6.

Examples of ionizing ionic compounds or multi-component reactive systems capable of producing an ionic catalytic system by reaction with a complex having formula (II) according to the present invention, are described, although with reference to the formation of ionic metallocene complexes, in the following publications, whose content is incorporated herein as reference:

W. Beck et al., Chemical Reviews, Vol. 88 (1988), pages 1405–1421;
S. H. Stares, Chemical Reviews, Vol. 93 (1993), pages 927–942;
Published European patent applications Nr.: EP-A 277,003, EP-A 495,375, EP-A 520,732, EP-A 427,697, EP-A 421, 659, EP-A 418,044;
Published international patent applications Nr.: WO 92/00333, WO 92/05208.

It has been found that the behaviour and reactivity of these ionic activator systems towards complexes having formula (II) is essentially analogous to that observed in the case of metallocene complexes of Ti and Zr used as catalysts in the polymerization of olefins. The specific characteristics of the catalytic system, in accordance with the present invention, should therefore be considered as being essentially due to the presence of the complex having formula (II), or to the products deriving therefrom, during the formation of the activated catalytic system.

Compounds having a fluorene structure described in patent application EP-A-1,013,675 filed by the same applicant, can also be used as cocatalysts (B) in the complexes having general formula (II).

As specified above, the catalytic system consists of the complex having general formula (II), as such or supported on an inert material, and a cocatalyst, preferably MAO (methylaluminoxane). The catalytic system can be prepared outside the oligomerization environment or in situ, i.e. inside the oligomerization reactor. The addition order of the two components is not critical.

The process of the present invention is carried out by putting ethylene, or a gas containing ethylene, in contact with the catalytic system described above, under certain pressure and temperature conditions, preferably in the presence of a solvent and/or diluent. In the preferred embodiment, a solvent/diluent selected from aliphatic, aromatic and cycloaliphatic hydrocarbons, preferably having from 3 to 8 carbon atoms, is used.

The gas containing ethylene which can be used in the process of the present invention comprises an inert gas containing ethylene, polymerization grade ethylene (for example high purity ethylene). In the preferred embodiment, the process of the present invention uses high purity ethylene.

The temperature of the process of the present invention ranges from 5° C. to 200° C., preferably from 20° C. to 80° C.

As far as the pressure is concerned, this is usually lower than 100 Kg/cm$^2$ (gauge pressure), preferably from 0.5 bars to 70 bars, even more preferably from 1 to 10 bars.

In the preferred embodiment, the catalytic system and ethylene are charged at the desired pressure, and the pressure is kept constant during the oligomerization reaction.

The reaction products prevalently consist of 1-butene, 1-hexene and 1-octene, prevalently 1-butene and 1-hexene.

The α-olefins thus produced can be separated from the reaction raw product according to methods known to experts in the field, particularly by means of distillation.

The following examples are provided for a better understanding of the present invention.

EXAMPLES

Tests 1–6

The tests are effected following the procedure described in example 1, varying the complex having general formula (II) (called precatalyst in the table) and/or the ethylene pressure. The results are summarized in Table 1.

Example 1

0.8 ml of MAO (10% w/w in toluene) are added, in a stream of nitrogen, to a suspension of 0.012 g (0.024 mmoles) of precatalyst BC05 in 150 ml of deaerated toluene. A light yellow-green solution is immediately formed. 5 ml of this solution are then placed in another flask containing 145 ml of deaerated toluene and 0.8 ml of MAO (10% w/w in toluene) and the whole mixture is transferred, by means of a cannula, to a 300 ml autoclave previously kept for 1 h under vacuum at room temperature. 60 psi (=412 kPa) of ethylene are then charged, at room temperature, into the latter, and the whole mixture is stirred by means of a mechanical stirrer (1500 revs/min). The pressure is kept constant (60 psi=412 kPa) for the whole duration of the test. After 30 minutes the stirring is stopped, the reaction mixture is brought to 0° C. by means of a bath containing ice and NaCl, the autoclave is depressurized and 10 ml of MeOH are added. At the end of the catalysis a ΔT of 5° C. and a Δp of 3.75 atm (390.2 kPa) are registered. A sample of the solution is analyzed by means of gaschromatography.

Internal Standard for the Gaschromatographic Analyses: N-Heptane.

The instrumentation used for the analysis of the oligomers (C$_4$ not quantified directly, calibration lines for 1-hexene and 1-octene): GC Shimadzu GC-14 A with a flame ionization detector. GC-MS Shimadzu QP 5000).

TABLE 1

| | Ethylene oligomerization tests | | | | | |
|---|---|---|---|---|---|---|
| pre-catalyst | test | P(C$_2$H$_4$) | ΔP Mpa | ΔT ° C. | C$_6$/C$_8$ | TOF (C$_6$, C$_8$) (mmol C$_2$H$_4$/mmol Mt-h) |
| | 1 | 60 psi | 0.39 | 5 | 9.7 | 45340 |
| | 2 | 200 psi | 1.98 | 17 | 11.3 | 197000 |

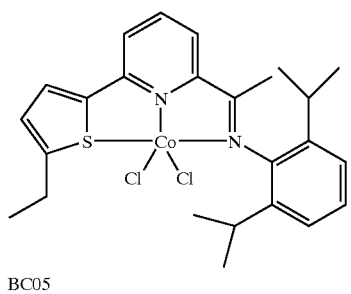

BC05

TABLE 1-continued

Ethylene oligomerization tests

| pre-catalyst | test | P(C$_2$H$_4$) | ΔP Mpa | ΔT °C. | C$_6$/C$_8$ | TOF (C$_6$, C$_8$) (mmol C$_2$H$_4$/mmol Mt-h) |
|---|---|---|---|---|---|---|
| 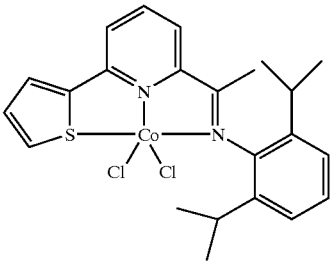 BC03 | 3 | 60 psi | 0.35 | 5 | 21.58 | 41220 |
|  | 4 | 200 psi | 2.35 | 23 | 15.52 | 191000 |
| 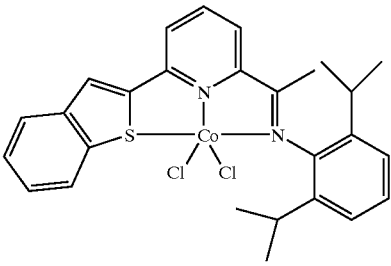 BC07 | 5 | 60 psi | 0.3 | 4 | 6.8 | 44171 |
|  | 6 | 200 psi | 3 | 21 | 5.3 | 439781 |

The results indicated in Table 1 show that whereas at 60 psi the activity (expressed as TOF) is equivalent for the three different catalysts, on passing to 200 psi there is a distinct increase in the activity for the complex BC 07. All three complexes however are extremely selective with the production essentially of butene, hexene and octene at a low pressure and at room temperature. This process therefore has a great advantage over the Shell, Idemitsu and Phillips processes which require more drastic conditions (for example: high pressures and temperatures). With respect to the system illustrated by Brookhart, ours undoubtedly has the advantage of being much more selective. Brookhart's catalytic system in fact leads to the formation not only of butene, hexene and octene but also higher homologous products up to the formation of waxes.

Example 7

0.025 mmoles of the complex BC03 dissolved in 150 ml of anhydrous toluene followed by 0.85 ml of MAO (1.57 M solution in toluene) (ratio Al/Co=50), are charged (after effecting the vacuum-nitrogen operation at least three times over a period of two hours and under static vacuum conditions), into a 300 ml volume Buchi glass autoclave, equipped with a propeller stirrer, valve for the gas inlet, thermocouple jacket and valve for charging the solutions containing the components of the catalytic system. At this point the stirring is started and the autoclave is pressurized with ethylene at 0.7 MPa, the pressure being kept constant for the whole duration of the test. The temperature increases from the initial 23° C. to 46° C. after 30 minutes with a ΔT of 23° C. At this stage, the autoclave is cooled as described in example 1. The gases at the head are recovered by bubbling them into two traps in series containing toluene and cooled to −60° C. A sample of the solution is analyzed by means of gaschromatography. The autoclave is depressurized and the polymerization stopped by the addition of 20 ml of methanol. A sample of the solution is analyzed by means of gaschromatography. Internal standard for the gaschromatographic analyses: n-dodecane.

Instrumentation Used for the Analysis of the Oligomers:

GC Hewlett Packard GC-5890 with a flame ionization detector; column: molten silica capillary of the PONA HP type, 50 m long, with an internal diameter of 0.2 mm, a film thickness of 0.5 mm; operating temperature: programmed from −5° C. for 7 min, increasing by 6° C. a minute up to 200° C., for 20 min (to obtain the initial temperature of −5° C., the gaschromatograph must be equipped with a cryogenic cooling plant fed with liquid nitrogen or carbon dioxide; flame ionization detector (F.I.D.); temperature 275° C.; carrier gas: hydrogen (pressure 130 Kpa); Injector: split (T: 220° C.), flow-rate 1.5 ml/min; splitting ratio 1:50. GC-MS Finnegan Inkos 50). The results of the analysis are indicated in Table 2.

TABLE 2

Ethylene oligomerization test

| pre-catalyst | test | $P(C_2H_4)$ | $\Delta T$ °C. | $C_4/C_6$ | $C_6/C_8$ | TOF (mmol $C_2H_4$/mmol Mt.h) |
|---|---|---|---|---|---|---|
| 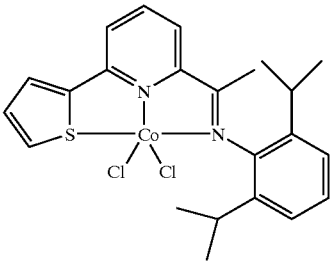 BC03 | 7 | 0.7 MPa | 23 | 5 | 7 | 81000 |

What is claimed is:

1. A process for the selective oligomerization of ethylene to give essentially $C_4$–$C_8$ α-olefins, characterized in that it is carried out in the presence of a catalytic system comprising the complex having general formula (II)

$$(L)M(Y)_n \quad (II)$$

wherein

L represents the ligand having general formula (I)

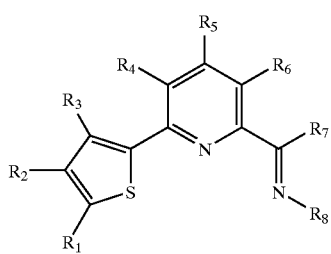

wherein $R_1$, $R_2$, $R_3$, $R_4$, $R_5$, $R_6$, the same or different, are selected from hydrogen, halogen, $C_1$–$C_{10}$ alkyl, $C_6$–$C_{15}$ aryl optionally halogenated, or adjacent pairs of $R_i$ groups (with i ranging from 1 to 6) are bound to each other to give cyclic hydrocarbon structures condensed with the thiophene or pyridine ring;

$R_7$ is selected from H, $C_1$–$C_{10}$ alkyl, $C_6$–$C_{15}$ aryl;

$R_8$ is selected from $C_1$–$C_{10}$ alkyl and $C_6$–$C_{15}$ aryl;

M is a metal selected from transition metals, i.e. metals of groups 3 to 12 of the periodic table, and lanthanides;

the above metal M being in oxidation state "s" positive different from zero, generally between 1 and 4;

Y is selected from groups of an anionic nature bound to the metal as anion in ionic couple or with a covalent bond of the "σ" type;

n expresses the number of Y groups sufficient for neutralizing the formal oxidation charge "s" of the metal M.

2. The process according to claim 1, wherein $R_3$=$R_4$=$R_5$=$R_6$=H, $R_7$=$C_1$–$C_{10}$ alkyl; $R_8$=phenyl as such or alkyl substituted.

3. The process according to claim 1, wherein M is a metal selected from metals of groups 4 to 10 of the periodic table.

4. The process according to claim 3, wherein M is a metal selected from Cobalt and Iron in oxidation state +2.

5. The process according to claim 1, wherein Y is selected from chlorine, bromine, alkoxide and carboxylate (having from 2 to 15 carbon atoms).

6. The process according to claim 1, characterized in that the catalytic system comprises, in addition to the complex having general formula (II), a cocatalyst, compound (B), essentially consisting of at least one organic compound of an element M' different from carbon and selected from elements of groups 2, 12, 13 or 14 of the periodic table.

7. The process according to claim 6, characterized in that the element M' is selected from boron, aluminum, zinc, magnesium, gallium and tin.

8. The process according to claim 7, characterized in that the element M' is selected from boron and aluminum.

9. The process according to claim 1, characterized in that the oligomerization takes place at a temperature ranging from 5° C. to 200° C., and at a pressure lower than 100 Kg/cm$^2$.

10. The process according to claim 9, characterized in that the temperature ranges from 20° C. to 80° C.

11. The process according to claim 9, characterized in that the pressure ranges from 0.5 bars to 70 bars.

12. The process according to claim 11, characterized in that the pressure ranges from 1 to 10 bars.

* * * * *